(12) United States Patent
Arthur et al.

(10) Patent No.: US 7,199,272 B2
(45) Date of Patent: Apr. 3, 2007

(54) METHOD FOR PREPARING PARA-(2-HYDROXYALKYLOXY) STYRENE MONOMERS AND OLIGOMERS

(75) Inventors: Samuel David Arthur, Wilmington, DE (US); Keith Kunitsky, West Grove, PA (US); Barry M. Trost, Los Altos Hills, CA (US); Mark E. Wagman, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 272 days.

(21) Appl. No.: 11/057,589

(22) Filed: Feb. 14, 2005

(65) Prior Publication Data
US 2005/0234266 A1 Oct. 20, 2005

Related U.S. Application Data

(60) Provisional application No. 60/545,888, filed on Feb. 19, 2004.

(51) Int. Cl.
*C07C 41/03* (2006.01)
(52) U.S. Cl. .................................... 568/608; 568/654
(58) Field of Classification Search ................ 568/608, 568/654
See application file for complete search history.

(56) References Cited

U.S. PATENT DOCUMENTS

| | | | |
|---|---|---|---|
| 4,680,358 A * | 7/1987 | Yu ........................... | 526/292.9 |
| 5,019,629 A | 5/1991 | Woods et al. | |
| 5,087,772 A | 2/1992 | Sheehan et al. | |
| 5,141,970 A | 8/1992 | McArdle et al. | |
| 5,156,771 A | 10/1992 | Yamamoto et al. | |
| 5,246,507 A | 9/1993 | Kodama et al. | |
| 5,633,411 A * | 5/1997 | Woods et al. ............... | 568/654 |
| 5,665,841 A | 9/1997 | Miller et al. | |
| 6,096,234 A | 8/2000 | Nakanishi et al. | |
| 6,111,146 A | 8/2000 | Rayborn | |
| 6,340,759 B1 | 1/2002 | Ueno et al. | |

FOREIGN PATENT DOCUMENTS

WO WO 03/025033 A2 3/2003

OTHER PUBLICATIONS

Ming-Qing et al., Graft Copolymers Having Hydrophobic Backbone and Hydrophilic Branches. XXIII. Particle Size Control of Poly(ethylene glycol)-Coated Polystyrene Nanoparticles Prepared by Macromonomer Method, Journal of Polymer Science: Part A: Polymer Chemistry, vol. 37:2155-2166, no month provided, 1999.
David Parker et al., Synthesis, Structure, and Properties of Hyberbranched Polyesters Based on Dimethyl 5-(2-Hydroxyethoxy)isophthalate, Macromolecules, vol. 34:2048-2059, Feb. 21, 2001.
Seiichi Inokuma et al., Synthesis of Thiacrownophanes Exhibiting High Ag+ Selectivities on the Liquid-Liquid Extraction, Heterocycles, vol. 40(1):401-411, no month provided, 1995.
Seiichi Inokuma et al., Synthesis of Pyridinocrownophanes Exhibiting High Ag+-Affinity, Heterocycles, vol. 54(1):123-130,no month provided, 2001.
Shoji Mori et al., New Gem-Dicyanocyclobutane-Containing Hydroxyesters, Journal of Polymer Science:Part A: Polymer Chemistry, vol. 28:551-558, no month provided, 1990.

* cited by examiner

*Primary Examiner*—Rosalynd Keys

(57) ABSTRACT

A method for preparing p-(2-hydroxyalkyloxy)styrene monomers and oligomers is described. The method comprises a base-catalyzed reaction of a styrene ester, a suitable alcohol and an alkylene oxide in a single vessel reaction. In this method, the reactive p-hydroxystyrene is generated in situ via the base-catalyzed transesterification reaction between the styrene ester and the alcohol in the presence of the base catalyst. The p-hydroxystyrene formed reacts with the alkylene oxide to form the p-(2-hydroxyalkyloxy)styrene monomer or oligomer.

19 Claims, No Drawings

US 7,199,272 B2

METHOD FOR PREPARING PARA-(2-HYDROXYALKYLOXY) STYRENE MONOMERS AND OLIGOMERS

This application claims the benefit of U.S. Provisional Applications 60/545,888, filed Feb. 19, 2004.

FIELD OF INVENTION

The invention relates to the field of organic synthesis. More specifically, the invention relates to a method for preparing p-(2-hydroxyalkyloxy)styrene monomers and oligomers from various styrene esters, a suitable alcohol, a suitable base catalyst and an alkylene oxide in a single vessel reaction.

BACKGROUND OF THE INVENTION

Para-(2-hydroxyalkyloxy)styrene monomers and oligomers, such as p-(2-hydroxyethoxy)styrene (pHES) and oligomers thereof, are well known compounds that have various applications as monomers. For example, p-(2-hydroxyalkyloxy)styrene monomers and oligomers are useful as monomers for the preparation of cross-linked polymer solid electrolytes (Nakanishi et al., U.S. Pat. No. 6,096,234), poly(ethylene glycol)-coated polystyrene nanoparticles (Chen et al., *J. Polym. Sci. Part A, Polym. Chem.* 37:2155–2166 (1999)), polymeric solid phase supports used for the synthesis of organic molecules (Sutherland et al., WO 03/025033), polymers for use as organic binders in electrically conductive pastes (Yamamoto et al., U.S. Pat. No. 5,156,771), polymers for the treatment of metal surfaces to prevent corrosion (Kodama et al., U.S. Pat. No. 5,246,507), as well as other applications.

Although various methods for preparing p-(2-hydroxyalkyloxy)styrene monomers and oligomers are known, these methods are not commercially feasible for large-scale production because they use starting materials that are difficult to work with or involve multistep reactions that are not performed in a single reaction vessel. For example, Inokuma et al. (*Heterocycles* 40:401–411 (1995)) describe the preparation of pHES by reacting para-hydroxystyrene (pHS) with 2-chloroethanol in aqueous sodium hydroxide solution. Mori et al. (*J. Polym. Sci. Part A, Polym. Chem.* 28:551–558 (1990)) describe the preparation of pHES from pHS. In that method, the pHS is first reacted with β-bromoethyl acetate under basic conditions to form p-(β-acetoxyethoxy)styrene, which is then treated with alkaline methanol to form pHES. The methods described in both of those disclosures use pHS as a starting material, which has several disadvantages. Para-hydroxystyrene is only available as a 10% by weight solution in propylene glycol from non-bulk commercial sources. This low initial concentration makes it difficult to use for scale-up purposes. Moreover, the use of pHS is complicated because it readily decomposes, is toxic via skin absorption, and it readily polymerizes.

Chen et al., supra describe a method for preparing p-(2-hydroxyethoxy)styrene oligomers from p-chloromethylstyrene and hydroxy group-terminated poly(ethylene glycol). In that method, p-chloromethylstyrene is mixed with sodium hydride in THF for 2 hours. Then, a hydroxy group-terminated poly(ethylene glycol) is added. The use of p-chloromethylstyrene as starting material has many of the disadvantages given above for pHS.

Inokuma et al. (*Heterocycles* 54:123–130 (2001)) describe the preparation of p-(2-hydroxyethoxy)styrene monomer and oligomers from a reaction utilizing oligoethyleneglycol mono(p-bromophenyl) ethers, tributylvinylstannane, and 2,6-di-tert-butyl-4-methylphenol in the presence of a tetrakis(triphenylphosphine) palladium catalyst.

Sutherland et al. supra describe a two-step procedure for preparing p-(2-hydroxyethoxy)styrene oligomers. In the first step, an oligo(ethylene glycol) ether is reacted with tosyl chloride to form the mono-tosyl-oligo(ethylene glycol) ether. In the second step, the isolated mono-tosyl-oligo (ethylene glycol) ether is reacted with p-acetoxystyrene to give the p-(2-hydroxyethoxy)styrene oligomer.

Woods et al. (U.S. Pat. No. 5,019,629) describe a two-step procedure for preparing p-(2-hydroxyethoxy)styrene starting with p-hydroxybenzaldehyde. In the first step, p-(2-hydroxyethoxy)benzaldehyde is formed by reacting p-hydroxybenzaldehyde with ethylene carbonate in the presence of potassium carbonate. In the second step, p-(2-hydroxyethoxy)styrene is formed by reacting the isolated p-(2-hydroxyethoxy)benzaldehyde with methyltriphenylphosphonium bromide in the presence of sodium amide.

Ueno et al. (U.S. Pat. No. 6,340,759) also describe a two-step procedure for preparing p-(2-hydroxyethoxy)styrene starting with p-hydroxybenzaldehyde. In the first step, p-(2-hydroxyethoxy)benzaldehyde is formed by reacting p-hydroxybenzaldehyde, sodium hydride, and (2-bromoethoxy)-tert-butyldimethylsilane. In the second step, p-(2-hydroxyethoxy)styrene is formed by reacting the isolated p-(2-hydroxyethoxy)benzaldehyde with (ethyl)triphenylphosphonium bromide in the presence of sodium hydride.

Sheehan et al. (U.S. Pat. No. 5,087,772) describe a method for preparing p-hydroxystyrene by reacting p-acetoxystyrene with a suitable alcohol in the presence of a catalytic amount of base. The preparation of p-(2-hydroxyalkyloxy)styrene monomers and oligomers is not described in that disclosure.

Methods for alkoxylating a phenolic substrate are known. Parker et al. (*Macromolecules* 34:2048–2059 (2001)) describe a process for the synthesis of dimethyl 5-(2-hydroxyethoxy)isophthalate by reacting dimethyl 5-hydroxyisophthalate with ethylene oxide in the presence of sodium methoxide. Rayborn (U.S. Pat. No. 6,111,146) describes the alkoxylation of an alkylphenol with an alkylene oxide using a base catalyst. Neither of those disclosures describes the preparation of p-(2-hydroxyalkyloxy)styrene monomers and oligomers in a single vessel reaction via a base-catalyzed reaction of a styrene ester, a suitable alcohol and an alkylene oxide.

The problem to be solved, therefore, is the need for an economical method for the large-scale, commercial production of p-(2-hydroxyalkyloxy)styrene monomers and oligomers. Additionally, the method should utilize starting reagents that are readily available and are stable and less toxic than those currently known in the art.

Applicants have solved the stated problem by discovering a method for producing p-(2-hydroxyalkyloxy)styrene monomers and oligomers via a base-catalyzed reaction of a styrene ester, a suitable alcohol and an alkylene oxide in a single vessel reaction.

SUMMARY OF THE INVENTION

The invention provides a method for preparing p-(2-hydroxyalkyloxy)styrene monomer comprising:
 a) providing in a single reaction vessel:
  i) an effective amount of a substrate having the general formula:

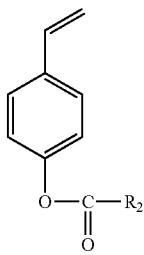

wherein R$_2$ is H, an alkyl group having from 1 to 20 carbon atoms, or phenyl;

ii) an effective amount of an alcohol;
  iii) an effective amount of a base catalyst; and
  iv) an effective amount of an alkylene oxide for producing the monomer comprising a mole ratio of alkylene oxide to substrate of from about 1:1 to about 2:1;

to form a reaction mixture;

b) heating the reaction mixture of step (a) at a temperature of from about 45° C. to about 160° C. and under a pressure of from atmospheric pressure to about 1000 psi wherein p-(2-hydroxyalkyloxy)styrene monomer is produced; and c) optionally recovering the p-(2-hydroxyalkyloxy)styrene monomer.

The invention also provides a method for preparing p-(2-hydroxyalkyloxy)styrene oligomer comprising:

a) providing in a single reaction vessel:
  i) an effective amount of a substrate having the general formula:

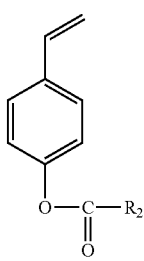

wherein R$_2$ is H, an alkyl group having from 1 to 20 carbon atoms, or phenyl;

ii) an effective amount of an alcohol;
  iii) an effective amount of a base catalyst; and
  iv) an effective amount of an alkylene oxide for producing the oligomer comprising a mole ratio of alkylene oxide to substrate of from about 2:1 to about 1000:1;

to form a reaction mixture;

b) heating the reaction mixture of step (a) at a temperature of from about 45° C. to about 160° C. and under a pressure of from atmospheric pressure to about 1000 psi wherein p-(2-hydroxyalkyloxy)styrene oligomer is produced having the general formula:

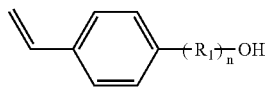

wherein n is 2 to about 1000, and R$_1$ is selected from the group consisting of O—(CH$_2$)$_2$, O—CH$_2$—CH(CH$_3$), O—CH$_2$—CH(CH$_2$CH$_3$), and mixtures thereof; and c) optionally recovering the p-(2-hydroxyalkyloxy)styrene oligomer.

DETAILED DESCRIPTION OF THE INVENTION

The invention provides a method for preparing p-(2-hydroxyalkyloxy)styrene monomers and oligomers via a base-catalyzed reaction of a styrene ester, a suitable alcohol and an alkylene oxide in a single vessel reaction. This method utilizes starting materials that are readily available, stable and less toxic than those known in the art. Additionally, the method of the present invention may be used for the large-scale production of p-(2-hydroxyalkyloxy)styrene monomers and oligomers with high yield. The method is useful because p-(2-hydroxyalkyloxy)styrene monomers and oligomers have application in the preparation of cross-linked polymer solid electrolytes, poly(ethylene glycol)-coated polystyrene nanoparticles, polymeric solid phase supports used for the synthesis of organic molecules, polymers for use as organic binders in electrically conductive pastes, polymers for the treatment of metal surfaces to prevent corrosion, as well as other applications.

The following definitions are used herein and should be referred to for interpretation of the claims and the specification.

"p" means para.

"pAS" is the abbreviation used for para-acetoxystyrene which is also represented as p-acetoxystyrene.

"pHS" is the abbreviation used for para-hydroxystyrene which is also represented as p-hydroxystyrene.

"pHES" is the abbreviation used for para-(2-hydroxyethoxy)styrene which is also represented as p-(2-hydroxyethoxy)styrene.

"psi" means pounds per square inch.

The term "oligomer" refers to a polymer comprising 2 or more monomer units. As used herein, oligomers of p-(2-hydroxyalkyloxy)styrene refer to p-(2-hydroxyalkyloxy)styrene compounds having multiple alkylene oxide units. Monomers of p-(2-hydroxyalkyloxy)styrene refer to p-(2-hydroxyalkyloxy)styrene compounds having one alkylene oxide unit.

The term "alkyl" refers to a straight or branched chain hydrocarbon containing no unsaturation.

All ranges given herein include the end of the ranges and also all the intermediate range points.

The instant invention comprises a method for producing p-(2-hydroxyalkyloxy)styrene monomers and oligomers having the general formula:

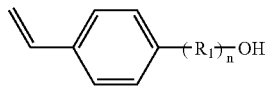

wherein $R_1$ is O—$(CH_2)_2$, O—$CH_2$—$CH(CH_3)$, O—$CH_2$—$CH(CH_2CH_3)$, or mixtures thereof, and n is 1 for the monomer and ranges from 2 to about 1000 for the oligomers, in addition ranges from 2 to about 100 for the oligomers. One product is p-(2-hydroxyethoxy)styrene, wherein $R_1$ is O—$(CH_2)_2$, and n=1. These monomers and oligomers are produced via a base-catalyzed reaction of an effective amount of a styrene ester, an effective amount of an alcohol and an effective amount of an alkylene oxide in the presence of an effective amount of a base catalyst in a single vessel reaction. In this method, the reactive p-hydroxystyrene (pHS) is generated in situ via a base-catalyzed transesterification reaction between the styrene ester and the alcohol in the presence of a suitable base catalyst. The pHS formed reacts with the alkylene oxide to form the p-(2-hydroxyalkyloxy)styrene monomer or oligomer.

The starting substrate in the reaction is a styrene ester having the general formula:

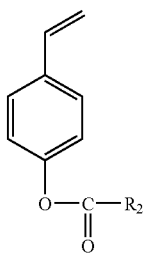

wherein $R_2$ is hydrogen (H), an alkyl group having from 1 to 20 carbon atoms, or phenyl. These substrates may be prepared using any method known in the art. For example, the alkyl styrene esters may be prepared using the method described by Overberger (U.S. Pat. No. 2,687,422, and *J. Amer. Chem. Soc.* 72:1200–1202 (1950)). The styrene ester wherein $R_2$=H (p-formylstyrene) may be prepared via the decarboxylation of p-formylcinnamic acid, as described by Wiley et al. (*J. Amer. Chem. Soc.* 71:2429–2431 (1949)). The styrene ester wherein $R_2$=phenyl (p-vinylphenol benzoate) may be prepared via the base-catalyzed addition of benzoyl chloride to p-hydroxystyrene, as described by Hattori et al. (*J. Amer. Chem. Soc.* 81:4424–4427 (1959)).

In one embodiment, the substrate is p-acetoxystyrene, wherein $R_2$ is $CH_3$. Para-acetoxystyrene (pAS) may be obtained in a number of ways. For example, pAS is available commercially in high purity from companies such as DuPont Electronic Polymers (Dallas, Tex.), Aldrich (Milwaukee, Wis.), Lancaster Synthesis (Pelham, N.H.), and TCI America (Portland, Ore.). Para-acetoxystyrene may also be synthesized according to the method described by Corson et al. (*J. Org. Chem.* 23:544 (1958)). Additionally, pAS may be obtained from pHS using the method described by Sounik et al. in U.S. Pat. No. 5,463,108. The pHS used as the starting material in that reaction may be produced by fermentation using a recombinant microorganism, as described by Ben-Bassat et al. (copending U.S. Patent Application No. 60/383,450, WO 03/099233 and copending U.S. Patent Application No. 60/462,827).

In the method of the present invention, the effective amount of substrate used in the reaction depends on several factors. The maximum effective amount of substrate is determined by its solubility in the alcohol used, infra. The minimum effective concentration of substrate is a practical consideration because the amount of product formed is related to the amount of substrate used in the reaction. Consequently, if the amount of substrate used is very low, very small amounts of the product will be produced. Higher concentrations of substrate also result in faster reaction kinetics, and therefore, shorter reaction times. Additionally, the effective amount of substrate depends upon the amount of suitable alcohol, described below, used in the reaction. The maximum amount of substrate should not exceed an equimolar amount of suitable alcohol. Therefore, the effective amount of substrate for the reaction may be readily determined by one of ordinary skill in the art based on the solubility of the particular substrate used, the requirements for reaction time, the amount of alcohol used, and the amount of product desired.

A suitable alcohol for use in the method of the present invention is an alcohol or a suitable mixture of alcohols having the formula $R_3OH$, wherein $R_3$ is an alkyl group having from 1 to 6 carbon atoms. The term "alkyl" refers to a straight or branched chain hydrocarbon containing no unsaturation. Examples of suitable alcohols include, but are not limited to, methyl alcohol, ethyl alcohol, propyl alcohol, isopropyl alcohol, butyl alcohol, 2-butyl alcohol, n-pentyl alcohol, n-hexyl alcohol, and mixtures thereof. The lower the molecular weight and the less branching of the alkyl group, $R_3$, the better is the alcohol in terms of the yield of the desired product. In one embodiment, the alcohol is methyl alcohol, ethyl alcohol, propyl alcohol, isopropyl alcohol or butyl alcohol. In another embodiment, the alcohol is methyl alcohol or ethyl alcohol.

The effective amount of suitable alcohol for use in the present invention ranges from about 1:1 to about 25:1 mole ratio of alcohol to substrate, in addition, ranges from about 10:1 to about 25:1 mole ratio of alcohol to substrate.

Suitable bases for use in the method of the present invention include inorganic bases, such as metal hydroxides; alkali metal hydroxides, such as potassium hydroxide, sodium hydroxide, lithium hydroxide, and cesium hydroxide; metal oxides, such as magnesium oxide and calcium oxide; alkali metal alkoxides, such as sodium methoxide, potassium methoxide, lithium methoxide, cesium methoxide, lithium ethoxide, sodium ethoxide, potassium ethoxide, cesium ethoxide, lithium isopropoxide, potassium isopropoxide, sodium isopropoxide, cesium isopropoxide, potassium tert-butoxide, and the like; organic ionic bases such as potassium acetate, potassium carbonate, and the like; and amines such as trimethylamine, triethylamine, tripropylamine, pyridine, and the like, which are soluble in the alcohol used. In one embodiment, a suitable mixture of any of the foregoing bases is used. In another embodiment, the base used for the preparation of p-(2-hydroxyalkyloxy) styrene monomer is potassium carbonate, potassium hydroxide, or sodium methoxide. In another embodiment, the base used for the preparation of p-(2-hydroxyalkyloxy)styrene monomer is potassium carbonate. In another embodiment, the base used for the preparation of p-(2-hydroxyalkyloxy) styrene oligomer is sodium hydroxide, potassium hydroxide, sodium methoxide or potassium methoxide.

The effective amount of suitable base is an amount of base that will optimize the yield of the desired product, at the time and temperature selected to run the reaction, with a minimum amount of polymerization of the pHS intermediate. This effective amount can be readily determined for the suitable alcohol, suitable base, time and temperature selected, by one of ordinary skill in the art without an undue amount of experimentation in light of the disclosure contained herein. Typically, an effective amount of a suitable base ranges from about 0.5 to about 10 mole percent relative to the substrate, in addition, ranges from about 3 to about 5 mole percent relative to the substrate. If much higher concentrations of base are used in the reaction, polymerization of the pHS intermediate may result, thereby reducing the yield of the desired product.

Suitable alkylene oxides for use in the method of the present invention include, but are not limited to, ethylene oxide, propylene oxide, butylene oxide, and mixtures thereof. The effective amount of alkylene oxide ranges from about 1:1 to about 1000:1 mole ratio of alkylene oxide to substrate, in addition, ranges from about 1:1 to about 100:1 mole ratio of alkylene oxide to substrate. The effective amount of alkylene oxide used in the reaction depends on the product desired. For example, the effective amount of alkylene oxide for producing the p-(2-hydroxyalkyloxy)styrene monomers is a mole ratio of alkylene oxide to substrate ranging from about 1:1 to about 2:1, in addition, a mole ratio of about 1.5:1 may be used. For p-(2-hydroxyalkyloxy) styrene oligomers, the mole ratio of alkylene oxide to substrate is adjusted to be approximately equal to the desired number of alkylene oxide units (n) in the oligomer. Specifically, the mole ratio of alkylene oxide to substrate for a desired n should be between about n to about n+1. For example, the effective amount of alkylene oxide to produce p-(2-hydroxyalkyloxy)styrene oligomer wherein n=2 is a mole ratio of alkylene oxide to substrate of from about 2:1 to about 3:1. Similarly, the effective amount of alkylene oxide to produce p-(2-hydroxyalkyloxy)styrene oligomer wherein n=20 is a mole ratio of alkylene oxide to substrate of from about 20:1 to about 21:1. It should be recognized that in the preparation of the p-(2-hydroxyalkyloxy)styrene oligomers, a mixture of oligomers will be obtained. The predominant oligomer formed will be that given by the mole ratio of alkylene oxide to substrate, as described above.

The effective amount of substrate, the effective amount of alcohol, the effective amount of base, and the effective amount of alkylene oxide, as described above, are mixed together in a single reaction vessel to form a reaction mixture. In another embodiment, the effective amount of substrate, the effective amount of alcohol, and the effective amount of base are mixed together in a single reaction vessel and the alkylene oxide is fed into the reaction vessel over a period of time, e.g., 2 to 12 hours, to form a reaction mixture. Any suitable reaction vessel may be used. A polymerization inhibitor, such as phenothiazine, p-methoxyphenol, or a nitroxide-containing inhibitor such as PROSTAB® 5415 (Ciba Specialty Chemicals, Tarrytown, N.Y.), may also be added to the reaction mixture to prevent polymerization of the substrate, the pHS intermediate, or the product. The reaction may be conducted at a temperature ranging from about 45° C. to about 160° C., in addition, ranging from about 85° C. to about 105° C., and further in addition at about 95° C., for a time sufficient to complete the reaction. The reaction may be carried out at a pressure ranging from atmospheric pressure to about 1000 psi, in addition, a pressure of about 100 psi may be used. The pressure may be adjusted using an inert gas such as nitrogen. For reactions at elevated pressures, any conventional pressure reaction vessel may be used including, but not limited to, shaker vessels, rocker vessels, and stirred autoclaves. After completion of the reaction, the alcohol and the ester formed by transesterification may be removed from the reaction vessel using any conventional method, such as evaporation under reduced pressure. If the product is a solid, it may be recrystallized from a suitable solvent such as toluene, benzene, or hexanes, at a temperature ranging from −78° C. to 25° C. Additionally, the product may be redissolved in an alcohol such as methanol and reprecipitated from solution by the addition of water to obtain the isolated product. If the product is an oil, the reaction mixture may be neutralized by the addition of an acid, such as acetic acid, and concentrated under reduced pressure to isolate the oil. Optionally, the oil may be purified using vacuum distillation or chromatographic techniques that are well known in the art.

The resultant p-(2-hydroxyalkyloxy)styrene monomer or oligomer may then be used in the preparation of cross-linked polymer solid electrolytes, poly(ethylene glycol)-coated polystyrene nanoparticles, polymeric solid phase supports used for the synthesis of organic molecules, polymers for use as organic binders in electrically conductive paste, polymers for the treatment of metal surfaces to prevent corrosion, and other applications, as previously described.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "mL" means milliliter(s), "L" means liter(s), "mol" means mole(s), "g" means gram(s), "ppm" means parts per million, "M" means molar concentration, "eq" means equivalents, "mp" means melting point, "GC" means gas chromatography, and "NMR" means nuclear magnetic resonance spectrometry, "IR" means infrared spectroscopy.

Example 1

Preparation of p-(2-Hydroxyethoxy)Styrene

The purpose of this Example was to prepare p-(2-hydroxyethoxy)styrene from p-acetoxystyrene, methanol, and ethylene oxide using potassium carbonate as base. The reaction was carried out using 2 M p-acetoxystyrene and a pressure of 100 psi.

A 1 L rocker pressure vessel was charged with 172 g (1.06 mol, 1 eq) of commercially available p-acetoxystyrene (obtained from DuPont Electronic Polymers, Dallas, Tex.), anhydrous methanol (530 mL), anhydrous potassium carbonate (7.4 g, 53.54 mmol, 0.05 eq), and ethylene oxide (70 g, 1.59 mol, 1.5 eq). The reaction was performed at 95° C. for 6 h under 100 psi $N_2$. The resulting light amber solution was concentrated under reduced pressure to produce an off-white solid. Water was added (1 L), and the solids were slurried for 30 min. The solids were filtered, washed with water (3 times), and dried on the filter under $N_2$. The solids were dissolved in toluene (8 mL/g), dried over $MgSO_4$, and filtered. The toluene solution was cooled overnight at −20° C. to produce a white precipitate, which was filtered (cold) through a coarse-fritted funnel, washed with 100 mL of cold toluene, and dried on the filter under $N_2$. The precipitate was dissolved in methylene chloride (5 mL/g), 50 ppm of the inhibitor 4-t-butylcatechol was added, and the solution was concentrated under reduced pressure. The precipitate was further dried in vacuo to afford the p-(2-hydroxyethoxystyrene) product as a white solid, 105.4 g (yield of 60.5%), mp 64–65° C. GC area %: 97.8; $^1$H NMR (400 MHz, $CDCl_3$):

δ (ppm) 7.34 (2H, ABq, J=6.6 Hz), 6.88 (2H, ABq, J=6.6 Hz), 6.66 (1H, dd, J=17.6 and 11.1 Hz), 5.61 (1H, dd, J=17.6 and 0.98 Hz), 5.13 (1H, dd J=11.1 and 0.98 Hz), 4.09 (2H, m), 3.96 (2H, m), 2.01 (1H, t).

Example 2

Preparation of p-(2-Hydroxyethoxy)Styrene

The purpose of this Example was to prepare p-(2-hydroxyethoxy)styrene from p-acetoxystyrene, methanol, and ethylene oxide using potassium carbonate as base. The reaction was carried out using 1 M p-acetoxystyrene and a pressure of 100 psi.

Para-(hydroxyethoxy)styrene was prepared using the method described in Example 1, except that the following amounts of reagents were used: 86 g (0.53 mol, 1 eq) of p-acetoxystyrene, 3.7 g (26.77 mmol, 0.05 eq) of anhydrous potassium carbonate, and 35 g (0.795 mol, 1.5 eq) of ethylene oxide in 530 mL of methanol. The isolated product yield was 61.9%.

Example 3

Preparation of p-(2-Hydroxyethoxy)Styrene

The purpose of this Example was to prepare p-(2-hydroxyethoxy)styrene from p-acetoxystyrene, methanol, and ethylene oxide using potassium carbonate as base. The reaction was carried out using 1 M p-acetoxystyrene and a pressure of 1000 psi.

Para-(hydroxyethoxy)styrene was prepared using the method described in Example 2, except that the reaction was performed under 1000 psi $N_2$. The isolated product yield was 66%.

Example 4

Preparation of p-(2-Hydroxyethoxy)Styrene

The purpose of this Example was to prepare p-(2-hydroxyethoxy)styrene from p-acetoxystyrene, methanol, and ethylene oxide using sodium methoxide as base. The reaction was carried out using 1 M p-acetoxystyrene and a pressure of 1000 psi.

A 400 mL shaker pressure vessel was charged with commercially available p-acetoxystyrene (10 g, 61.66 mmol, 1 eq), anhydrous methanol (60 mL), sodium methoxide (0.333 g, 6.164 mmol, 0.1 eq), and ethylene oxide (5 g, 113.5 mmol, 1.84 eq). The reaction was performed at 95° C. for 6 h under 1000 psi $N_2$. The formation of p-(2-hydroxyethoxy)styrene was confirmed by gas chromatography (50.1 GC area %). The p-(2-hydroxyethoxy)styrene was not isolated.

Example 5

Prophetic Example of the Preparation of oligo(ethylene glycol) mono(p-vinylphenyl)ether having 3 Ethylene Glycol Units The purpose of this prophetic Example is to describe how to prepare oligo(ethylene glycol) mono(p-vinylphenyl)ether having 3 ethylene glycol units (p-(2-hydroxyethoxy)styrene oligomer with n=3) from p-acetoxystyrene, methanol, and ethylene oxide using sodium methoxide as base. A mole ratio of ethylene oxide to p-acetoxystyrene of 4.0 is used in the reaction.

A 1 L stirred autoclave pressure vessel is charged with commercially available p-acetoxystyrene (86 g, 0.53 mol, 1 eq), methanol (265 mL), sodium methoxide (1.45 g, 0.0268 mol, 0.05 eq), and ethylene oxide (93.4 g, 2.12 mol, 4.0 eq). The reaction is performed at 95° C. for 6 h under 100 psi $N_2$. The resulting light amber solution is neutralized with acetic acid and concentrated under reduced pressure to produce a viscous oil. The product is purified by vacuum distillation. The inhibitor 4-t-butylcatechol (50 ppm) is added and the product is characterized by $^1$H NMR, $^{13}$C NMR, IR, and GC.

Example 6

Prophetic Example of the Preparation of oligo(propylene glycol)mono(p-vinylphenyl)ether having 20 Propylene Glycol Units The purpose of this prophetic Example is to describe how to prepare oligo(propylene glycol) mono(p-vinylphenyl) ether having 20 propylene glycol units (p-(2-hydroxypropoxy)styrene oligomer with n=20) from p-acetoxystyrene, methanol, and propylene oxide using sodium methoxide as base. A mole ratio of propylene oxide to p-acetoxystyrene of 21 is used in the reaction.

A 1 L stirred autoclave pressure vessel is charged with commercially available p-acetoxystyrene (32.45 g, 0.20 mol, 1 eq), methanol (100 mL), sodium methoxide (0.54 g, 0.0101 mol, 0.05 eq), and propylene oxide (243.6 g, 4.2 mol, 21 eq). The reaction is performed at 95° C. for 6 h under 100 psi $N_2$. The resulting light amber solution is neutralized with acetic acid and concentrated under reduced pressure to produce a viscous oil. The product is purified using vacuum distillation. The inhibitor 4-t-butylcatechol (50 ppm) is added and the product is characterized by $^1$H NMR, $^{13}$C NMR, IR, and GC.

What is claimed is:

1. A method for the production of p-(2-hydroxyalkyloxy) styrene monomer comprising:
   a) providing in a single reaction vessel:
      i) an effective amount of a substrate having the general formula:

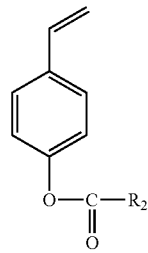

wherein $R_2$ is H, an alkyl group having from 1 to 20 carbon atoms, or phenyl;
   ii) an effective amount of an alcohol;
   iii) an effective amount of a base catalyst; and
   iv) an effective amount of an alkylene oxide for producing the monomer comprising a mole ratio of alkylene oxide to substrate of from about 1:1 to about 2:1;
   to form a reaction mixture;
   b) heating the reaction mixture of step (a) at a temperature of from about 45° C. to about 160° C. and under a pressure of from atmospheric pressure to about 1000 psi wherein p-(2-hydroxyalkyloxy)styrene monomer is produced; and c) optionally recovering the p-(2-hydroxyalkyloxy)styrene monomer.

2. A method for the production of p-(2-hydroxyalkyloxy) styrene oligomer comprising:

a) providing in a single reaction vessel:

i) an effective amount of a substrate having the general formula:

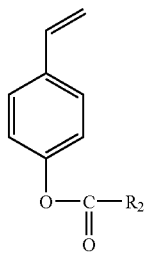

wherein $R_2$ is H, an alkyl group having from 1 to 20 carbon atoms, or phenyl;

ii) an effective amount of an alcohol;

iii) an effective amount of a base catalyst; and iv) an effective amount of an alkylene oxide for producing the oligomer comprising a mole ratio of alkylene oxide to substrate of from about 2:1 to about 1000:1;

to form a reaction mixture;

b) heating the reaction mixture of step (a) at a temperature of from about 45° C. to about 160° C. and under a pressure of from atmospheric pressure to about 1000 psi wherein p-(2-hydroxyalkyloxy)styrene oligomer is produced having the general formula:

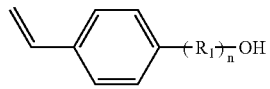

wherein n is 2 to about 1000, and $R_1$ is selected from the group consisting of O—$(CH_2)_2$, O—$CH_2$—CH($CH_3$), O—$CH_2$—CH($CH_2CH_3$), and mixtures thereof; and c) optionally recovering the p-(2-hydroxyalkyloxy)styrene oligomer.

3. A method according to either of claims 1 or 2 wherein the substrate is p-acetoxystyrene.

4. A method according to either of claims 1 or 2 wherein the alkylene oxide is selected from the group consisting of ethylene oxide, propylene oxide, butylene oxide, and mixtures thereof.

5. A method according to either of claims 1 or 2 wherein the base catalyst is selected from the group consisting of potassium carbonate, potassium hydroxide, sodium hydroxide, lithium hydroxide, cesium hydroxide, sodium methoxide, magnesium oxide, calcium oxide, potassium methoxide, lithium methoxide, cesium methoxide, potassium ethoxide, sodium ethoxide, lithium ethoxide, cesium ethoxide, potassium isopropoxide, sodium isopropoxide, lithium isopropoxide, cesium isopropoxide, potassium tert-butoxide, potassium acetate, trimethylamine, triethylamine, tripropylamine, pyridine, and mixtures thereof.

6. A method according to claim 1 wherein the base catalyst is selected from the group consisting of potassium carbonate, potassium hydroxide, sodium methoxide, and mixtures thereof.

7. A method according to claim 1 wherein the base catalyst is potassium carbonate.

8. A method according to claim 2 wherein the base catalyst is selected from the group consisting of sodium hydroxide, potassium hydroxide, sodium methoxide, potassium methoxide, and mixtures thereof.

9. A method according to either of claims 1 or 2 wherein the alcohol is selected from the group consisting of methyl alcohol, ethyl alcohol, propyl alcohol, isopropyl alcohol, butyl alcohol, 2-butyl alcohol, n-pentyl alcohol, n-hexyl alcohol and mixtures thereof.

10. A method according to either of claims 1 or 2 wherein the alcohol is selected from the group consisting of methyl alcohol, ethyl alcohol, and mixtures thereof.

11. A method according to either of claims 1 or 2 wherein the effective amount of alcohol is a mole ratio of alcohol to substrate of from about 1:1 to about 25:1.

12. A method according to either of claims 1 or 2 wherein the effective amount of alcohol is a mole ratio of alcohol to substrate of from about 10:1 to about 25:1.

13. A method according to either of claims 1 or 2 wherein the temperature is from about 85° C. to about 105° C.

14. A method according to either of claims 1 or 2 wherein the pressure is about 100 psi.

15. A method according to either of claims 1 or 2 wherein the effective amount of base catalyst ranges from about 0.5 mole percent to about 10 mole percent relative to the substrate.

16. A method according to either of claims 1 or 2 wherein the effective amount of base catalyst ranges from about 3 mole percent to about 5 mole percent relative to the substrate.

17. A method according to claim 1 wherein the p-(2-hydroxyalkyloxy)styrene monomer produced is p-(2-hydroxyethoxy)styrene.

18. A method according to either of claims 1 or 2 wherein said reaction mixture optionally comprises a polymerization inhibitor.

19. A method according to claim 18 wherein said polymerization inhibitor is selected from the group consisting of phenothiazine, p-methoxyphenol, and PROSTAB® 5415.

* * * * *